(12) United States Patent
Woessner et al.

(10) Patent No.: US 6,582,900 B1
(45) Date of Patent: Jun. 24, 2003

(54) METHODS FOR THE IDENTIFICATION OF MODULATORS OF MAGNESIUM CHELATASE EXPRESSION OR ACTIVITY IN PLANTS

(75) Inventors: Jeffrey P. Woessner, Hillsborough, NC (US); Adel Zayed, Durham, NC (US); Jörn Görlach, Durham, NC (US); Douglas C. Boyes, Chapel Hill, NC (US); Keith R. Davis, Durham, NC (US); Carol M. Hamilton, Apex, NC (US); Neil E. Hoffman, Chapel Hill, NC (US); Andreas S. Kloti, Durham, NC (US); Robert A. Ascenzi, Cary, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 318 days.

(21) Appl. No.: 09/659,310

(22) Filed: Sep. 12, 2000

(51) Int. Cl.$^7$ .............................. C12Q 1/00; C12Q 9/88; C12N 9/00; A01N 63/00
(52) U.S. Cl. ............................ 435/4; 435/183; 435/232; 435/262; 504/118
(58) Field of Search ........................ 435/4, 183, 232, 435/262; 504/118

(56) References Cited

FOREIGN PATENT DOCUMENTS

| DE | 19717656 A1 | 10/1998 |
|---|---|---|
| WO | 00/75340 | 12/2000 |

OTHER PUBLICATIONS

Gibson et al. Plant Physiol., 1996, vol. 111(1):61–71.*
Witkowski et al. Plant Physiol., 1988, vol. 87(3):632–637.*
Gibson, L. et al., "Magnesium–protoporphyrin chelatase of Rhodobacter sphaeroides: reconstruction of activity . . . ," "Proc.Natl.Acad.Sci., BioChemistry (US), vol. 92, p. 1941–1944, (Mar. 1995).
Jensen, P. et al., "Expression of the ch1I, ch1D, and ch1H Genes from the Cyanobacterium Synechocystis PCC6803 in *Escherichia coli* . . . ," The Am.Soc. for Biochem. and Mol. Bio, Inc. (US), vol. 271 ( No. 28), p. 16662–16667, ( Jul. 12, 1996).
Walker, C. et al., "Mechanism and regulation of Mg–chelatase," Biochem. J., (GB) vol. 327, p. 321–333, (1997).
Petersen, B. et al., "Reconstruction of an active magnesium chelatase enzyme complex from the bchI, –D, and –H gene products of the green sulfur . . . ," J. Bacteriol, Am.Soc.for Micro. (US), vol. 180 ( No. 3), p. 699–704, (Feb. 1998).
Willows, R. et al., "Heterologous expression of the Rhodobacter capsulatus BchI, –D, and –H genes that encode magnesium chelatase subunits and characterization of the reconstituted enzyme," J Biol Chem, The Am.Soc.for Biochem, and Mol. Bio. (US) vol. 273 (51), p. 34206–34213, (Dec. 18, 1998).
Gibson, L. et al., "Magnesium chelatase from Rhodobacter sphaeroides: initial characterization of the enzyme using purified subunits and evidence for a BchI–BchD complex," Biochem. J.,The Biochem Soc. (London), vol.337, p. 243–251, (1999).
Hansson, A. et al., "Molecular basis for semidominance of missence mutations in the XANTHA–H (42–kDa) subunit of magnesium chelatase," Plant Biology, Natl.Acad. Sci., vol. 96 ( No. 4), p.1744–1749, (Feb. 16, 1999).
Grafe, S. et al., "Mg–chelatase of tobacco: the role of the subunit CHL D in the chelation step of protoporphyrin IX," Proc.Natl.Acad.Sci., Biochemistry(US), vol. 96, p. 1941–1946, (Mar. 1999).
Wuebert, J. et al. "Hydroxybenzoic acid methylesters inhibit magnesium chelatase activity in cress and barley seedings"; Plant Physiology and Biochemistry (Paris), vol. 35 (8), 1997; pp. 581–587.

* cited by examiner

Primary Examiner—Rebecca E. Prouty
Assistant Examiner—Manjunath N. Rao
(74) Attorney, Agent, or Firm—Laura L. Kiefer; Timothy G. Hofmeyer; Deborah H. Spencer

(57) ABSTRACT

The present inventors have discovered that Mg-chelatase is essential for the growth of Arabidopsis. Specifically, the inhibition of Mg-chelatase CHL H gene expression in Arabidopsis seedlings results in varying levels of chlorosis (yellowing), significantly reduced growth and developmental abnormalities. Thus, Arabidopsis Mg-chelatase can be used as a target for the identification of herbicides. Accordingly, the present invention provides methods for the identification of compounds that modulate Arabidopsis Mg-chelatase expression or activity, comprising: contacting a compound with a Arabidopsis Mg-chelatase, or a subunit thereof, and detecting the presence and/or absence of binding between said compound and said Mg-chelatase, or detecting a change in Mg-chelatase expression or activity.

The methods of the invention are useful for the identification of herbicides and other compounds that can modulate plant growth and development. In addition, the methods of the invention are useful for the identification of compounds that stimulate the expression or function of Mg-chelatase expression or function. Such compounds can be used to promote or manipulate plant growth and development.

5 Claims, 2 Drawing Sheets

METHODS FOR THE IDENTIFICATION OF MODULATORS OF MAGNESIUM CHELATASE EXPRESSION OR ACTIVITY IN PLANTS

FIELD OF THE INVENTION

The invention relates generally to plant molecular biology. In particular, the invention relates to methods for the identification of compounds that regulate plant growth and development through the modulation of magnesium chelatase expression or activity.

BACKGROUND OF THE INVENTION

Magnesium chelatase (Mg-chelatase) is an enzyme involved in the synthesis of chlorophyll in plants and photosynthetic microorganisms, and of bacteriochlorophyll in photosynthetic bacteria. Specifically, Mg-chelatase catalyzes the ATP-dependent insertion of a magnesium ion into protoporphyrin IX, to form Mg-protoporphyrin IX. Protoporphyrin IX is the last common intermediate in chlorophyll, bacteriochlorophyll and heme biosynthesis. In all photosynthetic organisms studied to date, Mg-chelatase activity requires three subunits, which are commonly referred to as CHL D, CHL H and CHL I.

The Mg-chelatase reaction is thought to occur in two steps, preactivation and catalysis. Grafe et al. (1999) *Proc Natl Acad Sci* 96:1941–1946. According to the current model, in the preactivation step, a CHL D dimer associates with two CHL I monomers in the presence of $Mg^{2+}$ and ATP. In the chelation step, which involves the hydrolysis of ATP, the CHL H subunits interact with the CHL D subunits, resulting in the insertion of $Mg^{2+}$ into protoporphyrinogen IX. It is unclear whether the CHL I subunit remains associated with CHL D during the second step. Id.

The genes or cDNAs encoding Mg-chelatase subunits from a variety of plants and microorganisms have been cloned and expressed. In vitro Mg-chelatase activity has been demonstrated by reconstitution of the three subunits of tobacco Mg-chelatase. Mg-chelatase mutants have been identified in barley and tobacco. For example, several recessive lethal mutations have been isolated in each of the genes encoding the three barley Mg-chelatase subunits, Xantha-f, Xantha-g and Xantha-h. Henningsen et al. (1993) *R Dan Acad Sci Lett Biol Skr* 42:1–349; and Hansson et al. (1999) *Plant Biol* 96:1744–1749. A mutation resulting in a single amino acid residue substitution in the CHL I subunit of tobacco Mg-chelatase results in heterozygous plants with reduced levels of chlorophyll and a yellow-green phenotype, and homozygous yellow seedling lethals. Kjemtrump et al. (1998) *Plant J* 14:91–100. Antisense RNA expression of the Mg-chelatase CHL I or CHL H subunit of tobacco results in a decreased growth rate chlorophyll deficiency in transgenic tobacco plants. Papenbrock et al. (2000) *Plant J* 22:155–164; and Papenbrock et al. (2000)*Plant Physiol* 122:1161–1170. In Arabidopsis, a transposon insertion mutation in the CHL I subunit (chlorata-42), results in a fusion of the carboxy terminus of the CHL I subunit to a short open reading frame in the transposon. Chlorata-42 plants have a pale green phenotype. However, to date, no study has shown that Mg-chelatase is essential in Arabidopsis.

It has been suggested that inhibitors of plant Mg-chelatases may have potential herbicidal activity (German patent application DE 197 17 656). However, there are no herbicides that are known to act by modifying the activity of this enzyme. Accordingly, there is a need for assays that can be used to detect modulators of Mg-chelatase activity. Inhibitors of Mg-chelatase activity or expression have use as herbicides.

SUMMARY OF THE INVENTION

The present inventors have discovered that Mg-chelatase is essential for the growth of Arabidopsis. Specifically, the inhibition of Mg-chelatase CHL H gene expression in Arabidopsis seedlings results in varying levels of chlorosis (yellowing), significantly reduced growth and developmental abnormalities. Thus, Arabidopsis Mg-chelatase can be used as a target for the identification of herbicides. Accordingly, the present invention provides methods for the identification of compounds that modulate Arabidopsis Mg-chelatase expression or activity, comprising: contacting a compound with Arabidopsis Mg-chelatase, or a subunit thereof, and detecting the presence and/or absence of binding between said compound and said Mg-chelatase, or detecting a change in Mg-chelatase expression or activity.

The methods of the invention are useful for the identification of herbicides and other compounds that can modulate plant growth and development. In addition, the methods of the invention are useful for the identification of compounds that stimulate the expression or function of Mg-chelatase expression or function. Such compounds can be used to promote or manipulate plant growth and development.

DETAILED DESCRIPTION OF THE INVENTION

Definitions

Figure 1:
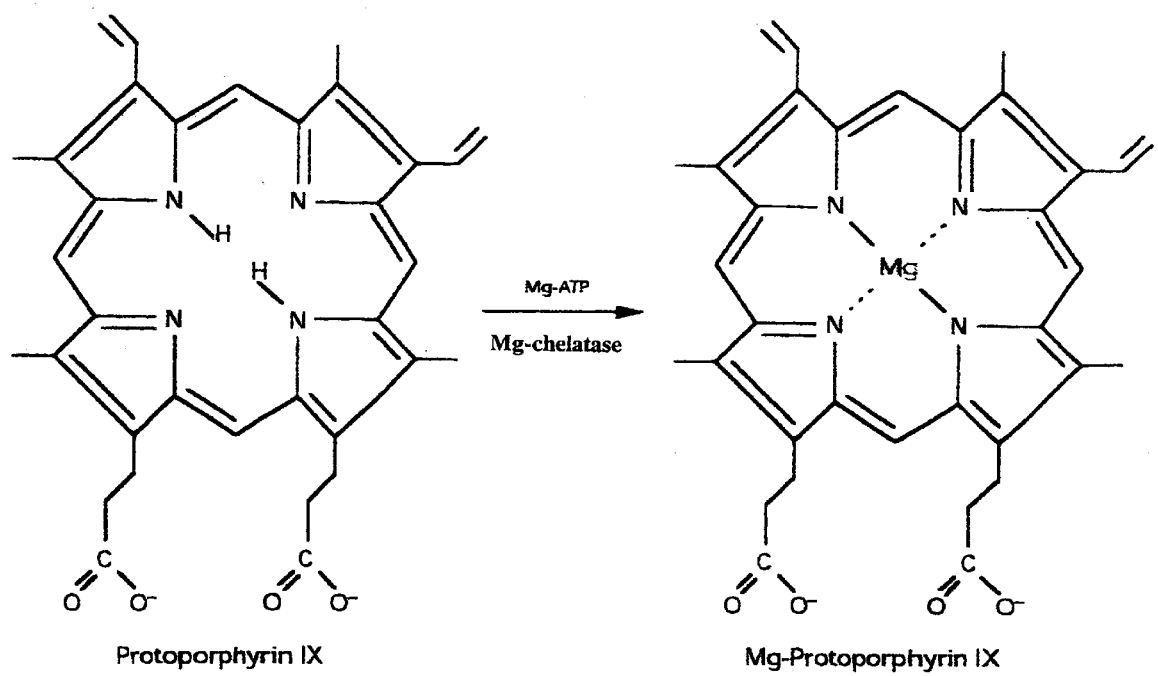
FIG. 1 shows the chemical structures of protoporphyrinogen IX and Mg-protoporphyrinogen LX.

The term "binding" refers to a noncovalent interaction that holds two molecules together. For example, two such molecules could be an enzyme and an inhibitor of that enzyme. Noncovalent interactions include hydrogen bonding, ionic interactions among charged groups, van der Waals interactions and hydrophobic interactions among non-polar groups. One or more of these interactions can mediate the binding of two molecules to each other.

The term "herbicide", as used herein, refers to a chemical that may be used to kill or suppress the growth of at least one plant, plant cell, plant tissue or seed.

By "herbicidally effective amount" is meant an amount of a chemical or composition sufficient to kill a plant or decrease plant growth and/or viability by at least 20%. More preferably, the growth or viability will be decreased by 25%, 50%, 75%, 80%, 90% or more.

The term "inhibitor", as used herein, refers to a chemical substance that inactivates the enzymatic activity of Mg-chelatase. The inhibitor may function by interacting directly with the enzyme or a subunit thereof, a cofactor of the enzyme, the substrate of the enzyme, or any combination thereof.

A polynucleotide may be "introduced" into a plant cell by any means, including transfection, transformation or transduction, electroporation, particle bombardment, agroinfection and the like. The introduced polynucleotide may be maintained in the cell stably if it is incorporated into a non-chromosomal autonomous replicon or integrated into the plant chromosome. Alternatively, the introduced polynucleotide may be present on an extra-chromosomal non-replicating vector and be transiently expressed or transiently active.

For the purposes of the invention, "ligand" refers to a molecule that will bind to a site on a polypeptide.

As used herein, the term "Mg-chelatase" is synonymous with "magnesium chelatase", "protoporphyrinogen Mg-chelatase", "protoporphyrinogen Mg-chelatase", "protoporphyrinogen IX Mg-chelatase", "Mg-protoporphyrinogen chelatase" and "Mg-protoporphyrinogen IX chelatase". Mg-chelatase catalyzes the insertion of $Mg^{2+}$ into protoporphyrinogen IX to yield Mg-protoporphyrinogen IX. Three subunits, CHL D, CHL H and CHL I, are required for Mg-chelatase activity. For the purposes of the invention, Mg-chelatase refers to a composition comprising these three subunits.

The "percent (%) sequence identity" between two polynucleotide or two polypeptide sequences is determined according to the either the BLAST program (Basic Local Alignment Search Tool; Altschul and Gish (1996) *Meth Enzymol* 266:460–480 and Altschul (1990) *J Mol Biol* 215:403–410) in the Wisconsin Genetics Software Package (Devererreux et al. (1984) *Nucl Acid Res* 12:387), Genetics Computer Group (GCG), Madison, Wis. (NCBI, Version 2.0.11, default settings) or using Smith Waterman Alignment (Smith and Waterman (1981) *Adv Appl Math* 2:482) as incorporated into GeneMatcher Plus™ (Paracel, Inc., http://www.paracel.com/html/genematcher.html; using the default settings and the version current at the time of filing). It is understood that for the purposes of determining sequence identity when comparing a DNA sequence to an RNA sequence, a thymine nucleotide is equivalent to a uracil nucleotide.

"Plant" refers to whole plants, plant organs and tissues (e.g., stems, roots, ovules, stamens, leaves, embryos, meristematic regions, callus tissue, gametophytes, sporophytes, pollen, microspores and the like) seeds, plant cells and the progeny thereof.

By "polypeptide" is meant a chain of at least four amino acids joined by peptide bonds. The chain may be linear, branched, circular or combinations thereof The polypeptides may contain amino acid analogs and other modifications, including, but not limited to glycosylated or phosphorylated residues.

The term "specific binding" refers to an interaction between Mg-chelatase or a subunit thereof, and a molecule or compound, wherein the interaction is dependent upon the primary amino acid sequence or the conformation of Mg-chelatase and/or the Mg-chelatase subunit.

Embodiments of the Invention

The present inventors have discovered that inhibition of the Mg-chelatase subunit CHL H gene expression strongly inhibits the growth and development of Arabidopsis plant seedlings. Thus, the inventors are the first to show that Arabidopsis Mg-chelatase is a target for herbicides.

Accordingly, the invention provides methods for identifying compounds that modulate Arabidopsis Mg-chelatase gene expression or activity. Such methods include ligand binding assays, assays for enzyme activity and assays for Arabidopsis Mg-chelatase gene expression. Any compound that is a ligand for Arabidopsis Mg-chelatase or a subunit thereof, other than its substrate or cofactors (i.e., protoporphyrinogen IX, $Mg^{2+}$ and ATP (adenosine 5'-triphosphate)) may have herbicidal activity. The compounds identified by the methods of the invention are useful for the modulation of plant growth and development.

Thus, in one embodiment, the invention provides a method for identifying a compound as a candidate for a herbicide, comprising:
a) contacting an Arabidopsis Mg-chelatase, or at least one subunit thereof, with said compound; and
b) detecting the presence and/or absence of binding between said compound and said Arabidopsis Mg-chelatase or subunit thereof;
wherein binding indicates that said compound is a candidate for a herbicide.

By "Arabidopsis Mg-chelatase" is meant any Arabidopsis enzyme that catalyzes the insertion of $Mg^{2+}$ into protoporphyrinogen IX to yield Mg-protoporphyringen IX. Three Mg-chelatase subunits, CHL D, CHL H and CHL I are required for this reaction. For the purposes of the invention, an Arabidopsis Mg-chelatase refers to a composition containing the CHL D, CHL H and CHL I Mg-chelatase subunits from an species of Arabidopsis. The Mg-chelatase subunits may have the amino acid sequences of naturally occuring Arabidopsis Mg-chelatase subunits, or may have at least 90% amino acid sequence identity with naturally occuring Arabidopsis Mg-chelatase subunit sequences. Preferably, the sequence identity is at least 92%, more preferably the identity is at least 95%, most preferably the sequence identity is at least 98%.

The Mg-chelatases useful in the methods of the invention can be from any species of Arabidopsis. Arabidopsis species include, but are not limited to, *Arabidopsis arenosa, Arabidopsis bursifolia, Arabidopsis cebennensis, Arabidopsis croatica, Arabidopsis griffithiana, Arabidopsis halleri, Arabidopsis himalaica, Arabidopsis korshinskyi, Arabidopsis lyrata, Arabidopsis neglecta, Arabidopsis pumila, Arabidopsis suecica, Arabidopsis thaliana* and *Arabidopsis wallichii*. Preferably, the Mg-chelatase is from *Arabidopsis thaliana*, most preferably from *Arabidopsis thaliana* strain Columbia. The amino acid sequences of the *Arabidopsis thaliana* Mg-chelatase subunits are publicly available. See, for example, GenBank Accession No. AF083555 (*A. thaliana* CHL D precursor amino acid sequence and mRNA); GenBank accession No. Z68495 and EMBase accession No. S71288 (*A. thaliana* CHL H amino acid sequence and mRNA); and EMBL Accession No. X51799 and Swiss-Prot Accession No. P16127 (*A. thaliana* CHL I amino acid sequence and mRNA).

Fragments of an Arabidopsis Mg-chelatase may be used in the methods of the invention. The fragments comprise at least 20 consecutive amino acids of an Arabidopsis Mg-chelatase subunit. Preferably, the fragment comprises at least 25, 30, 35 or at least 40 consecutive amino acids residues of an Arabidopsis Mg-chelatase subunit. Most preferably, the fragment comprises at least 20 consecutive amino acids of a conserved and/or functional region of a Mg-chelatase subunit. The consensus sequence for the CHL I subunits from *Crytomeronas phi, Methanococcus jannaschii, Arabidopsis thaliana, Euglena gracilis, Cyanophora paradoxa, Olisthodiscus luteus, Hordeum vulgare, Rhodobacter capsulatus,* Synechocystis sp. P.C.C. 6803, *Anabaena variablis, Odontella sinesis, Porphyra purpea* and *Glycine max* is reported in Walker et al. (1997) *Biochem J* 327:321–333. Functional regions of Mg-chelatase subunits are disclosed in Grafe et al. (1999) *Proc Natl Acad Sci* 96:1941–1946.

Thus, in another embodiment, the invention provides a method for identifying a compound as a candidate for a herbicide, comprising:
a) contacting said compound with at least one polypeptide selected from the group consisting of: an amino acid sequence comprising at least 20 consecutive amino acids of an Arabidopsis Mg-chelatase subunit and an amino acid sequence having at least 90% sequence identity with an Arabidopsis Mg-chelatase subunit; and b) detecting the presence and/or absence of binding between said compound and said polypeptide;

wherein binding indicates that said compound is a candidate for a herbicide.

Any technique for detecting the binding of a ligand to its target may be used in the methods of the invention. Preferably, the ligand and target are combined in a buffer. Polypeptides and proteins that can reduce non-specific binding, such as BSA or protein extracts from cells that do not produce the target, may be included in binding assay. $Mg^{2+}$ and ATP may also be included in the binding assay.

Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with one or more Mg-chelatase subunits or variants thereof, the unbound protein is removed and the bound Mg-chelatase subunit(s) is detected. In a preferred embodiment, bound Mg-chelatase is detected using a labeled binding partner, such as a labeled antibody. In a variation of this assay, a Mg-chelatase subunit is labeled prior to contacting the immobilized candidate ligands. Preferred labels include fluorescent or radioactive moieties. Preferred detection methods include fluorescence correlation spectroscopy (FCS) and FCS-related confocal nanofluorimetric methods.

Once a compound is identified as a candidate for a herbicide, it can be tested for the ability to inhibit or otherwise modulate Mg-chelatase enzyme activity. The compounds can be tested using either in vitro or cell based enzyme assays. Alternatively, a compound can be tested by applying it directly to a plant or plant cell, or expressing it therein, and monitoring the plant or plant cell for changes or decreases in growth, development, viability or alterations in gene expression.

Thus, in one embodiment, the invention provides a method for determining whether a compound identified as a herbicide candidate by an above method has herbicidal activity, comprising: contacting a plant or plant cells with said herbicide candidate and detecting the presence or absence of a decrease in the growth or viability of said plant or plant cells.

By decrease in growth, is meant that the herbicide candidate causes at least a 20% decrease in the growth of the plant or plant cells, as compared to the growth of the plants or plant cells in the absence of the herbicide candidate. By a decrease in viability is meant that at least 20% of the plants cells, or portion of the plant contacted with the herbicide candidate are nonviable. Preferably, the growth or viability will be at decreased by at least 25%. More preferably, the growth or viability will be decreased by at least 50%, 75% or at least 90% or more. Methods for measuring plant growth and cell viability are known to those skilled in the art. It is possible that a candidate compound may have herbicidal activity only for certain plants or certain plant species.

The ability of a compound to inhibit or modulate Mg-chelatase activity can be detected using in vitro enzymatic assays in which the disappearance of a substrate or the appearance of a product is directly or indirectly detected. Mg-chelatase catalyzes the insertion of $Mg^{2+}$ into protoporphyrinogen IX to yield Mg-protoporphyrinogen IX.

Thus, the invention provides a method for identifying a compound as a candidate for a herbicide, comprising:

a) contacting protoporphyrinogen IX with Mg-chelatase in the absence of said compound;

b) contacting protoporphyrinogen IX with Mg-chelatase in the presence of said compound; and c) determining the concentration of protoporphyrinogen IX and/or Mg-protoporphyrinogen IX after the contacting of steps (a) and (b);

wherein said Mg-chelatase is from Arabidopsis and said contacting is performed in the presence of $Mg^{2+}$ and ATP.

If a candidate compound inhibits Mg-chelatase activity, a higher concentration of the substrate (protoporphyrinogen IX) and a lower level of the product (Mg-protoporphyrinogen IX) will be detected in the presence of the candidate compound (step b) than in the absence of the compound (step a).

The contacting should occur under conditions suitable for Mg-chelatase activity. Methods for measuring protoporphyrinogen IX and Mg-protoporphyrinogen IX and Mg-chelatase activity are known in the art. Such methods include, but are not limited to, fluorometry, spectrophotometry, HPLC, TLC and mass spectroscopy. See, for example, Hansson et al. (1999) *Proc Natl Acad Sci* 96:1744–1749; Grafe et al. (1999) *Proc Natl Acad Sci* 96:1941–1946; Petersen et al. (1998) *J Bacteriol* 180:699–704; Gibson et al (1999) *Biochem J* 337:243–251; Willows et al. (1998) *J Biol Chem* 273:34206–34213 and Jensen et al. (1996) *J Biol Chem* 271:16662–16667.

Preferably, protoporphyrinogen IX and Mg-protoporphyrinogen IX are detected by fluorometry. The characteristic fluorescence maxima of protoporphyrinogen IX and Mg-protoporphyrinogen IX are 633 and 595 nm, respectively. Preferably, Mg-protoporphyrin is concentration is determined using a fluorescence detector with excitation at approximately 400–430 nm and emission at 580–605 nm. Protoporphyrin IX and ATP are available through a variety of chemical suppliers, including Sigma.

In one assay for Mg-chelatase activity, 100 ml buffer containing 50 mM Tricine/NaOH pH 7.9, 12 mM $MgCl_2$, 4 mM ATP, 6 μM protoporphyrinogen IX, 50 ng CHL D, 200 ng CHL I and 10 μg CHL H are incubated at 34° C. for 30 minutes. The reaction is stopped by the addition of 900 μl acetone/water/32% ammonia (80:20:1, vol/vol/vol) and centrifuged at 15,000 g for 5 minutes. The aqueous phase is analyzed by spectroflurometry with an excitation wavelength of 420 nm and recordation of the emission spectrum between 550 and 650 nm. See Gibson et al. (1999) *Biochem J* 337:243–251.

In another assay, Mg-chelatase subunits are added to 6 μM deuteroporphyrin IX, 5 mM ATP, 25 mM creatine kinase, 25 $MgCl_2$, 2.5 units creatine kinase, 20 mM Tris pH 9.0 in a volume of 50 μl, and incubated for 20 minutes at 30° C. The reaction is stopped by the addition of 1 ml acetone/water/ 25% ammonia (80:20:1, vol/vol/vol) and 200 μl hexane. The phases are then separated by brief centrifugation, and the emission spectrum of the bottom acetone phase is determined form 550 to 650 with an excitation wavelength of 408 nm. See Hansson et al. (1999) *Proc Natl Acad Sci* 96:1744–1749.

In a preferred fluorometric assay, fluorescence (420 excitation/596 nm emission) is monitored continuously in a reaction buffer containing 50 mM Tricine/NaOH pH 7.9, 10 mM $MgCl_2$, 1 mM DTT, 4 mM ATP, 6 μM protoporphyrinogen IX, 50 ng CHL D, 200 ng CHL I and 10 μg CHL H at 34° C. See Gibson et al. (1999) *Biochem J* 337:243–251.

For the in vitro enzymatic assays, Mg-chelatase and subunits thereof may be purified from Arabidopsis, expressed in an in vitro transcription/translation system, or may be recombinantly produced in and purified from a plant, bacteria, or eukaryotic cell culture. For example, His-tagged Mg-chelatase subunits have been over expressed in *E. coli* and purified over $Ni^{2+}$-agarose affinity columns. Petersen et al. (1998) *J Bacteriol* 180:699–704. Hansson et al. (1999) *Proc Natl Acad Sci* 96:1744–1749 describe a method for purifying Mg chelatase subunits from plant leaves. Additional methods for the purification of Mg-chelatase subunits are known to those skilled in the art. Preferably these proteins are produced using a baculovirus or yeast expression system.

As an alternative to in vitro assays, the invention also provides plant and plant cell based assays. In one embodiment, the invention provides a method for identifying a chemical as a candidate for a herbicide, comprising:
  a) measuring the expression of Mg-chelatase in an Arabidopsis plant or plant cell in the absence of said chemical;
  b) contacting an Arabidopsis plant or plant cell with said chemical and measuring the expression of Mg-chelatase in said plant or plant cell;
  c) comparing the expression of Mg-chelatase in steps (a) and (b).

A reduction in Mg-chelatase expression indicates that the compound is a herbicide candidate. In one embodiment, the plant or plant cell is an *Arabidopsis thaliana* plant or plant cell.

Expression of Mg-chelatase can be measured by detecting Mg-chelatase primary transcripts or mRNAs, Mg-chelatase enzyme or subunits or Mg-chelatase enzymatic activity. Methods for detecting the expression of RNA and proteins are known to those skilled in the art. See, for example, *Current Protocols in Molecular Biology* Ausubel et al., eds., Greene Publishing and Wiley-Interscience, New York, 1995. The method of detection is not critical to the invention. Methods for detecting Mg-chelatase RNA include, but are not limited to amplification assays such as quantitative PCR, and/or hybridization assays such as Northern analysis, dot blots, slot blots, in-situ hybridization, bDNA assays and microarray assays.

Methods for detecting protein expression include, but are not limited to, immunodetection methods such as Western blots, His-Tag and ELISA assays, polyacrylamide gel electrophoresis, mass spectroscopy and enzymatic assays. Also, any reporter gene system may be used to detect Mg-chelatase protein expression. For detection using gene reporter systems, a polynucleotide encoding a reporter protein is fused in frame with a Mg-chelatase subunit, so as to produce a chimeric polypeptide. Methods for using reporter systems are known to those skilled in the art. Examples of reporter genes include, but are not limited to, chloramphenicol acetyltransferase (Gorman et al. (1982) *Mol Cell Biol* 2:1104; Prost et al. (1986) Gene 45:107–111), β-galactosidase (Nolan et al. (1988) *Proc Natl Acad Sci USA* 85:2603–2607), alkaline phosphatase (Berger et al. (1988) *Gene* 66:10), luciferase (De Wet et al. (1987) *Mol Cell Biol* 7:725–737), β-glucuronidase (GUS), fluorescent proteins, chromogenic proteins and the like. Methods for detecting Mg-chelatase activity are described above.

Chemicals, compounds or compositions identified by the above methods as modulators of Mg-chelatase expression or activity can then be used to control plant growth. For example, compounds that inhibit plant growth can be applied to a plant or expressed in a plant, in order to prevent plant growth. Thus, the invention provides a method for inhibiting plant growth, comprising contacting a plant with a compound identified by the methods of the invention as having herbicidal activity. Alternatively, such compounds may be applied to or expressed in a particular plant tissue or organ so as to modulate growth of that tissue or organ.

Herbicides and herbicide candidates identified by the methods of the invention can be used to control the growth of undesired plants, including both monocots and dicots. Examples of undesired plants include, but are not limited to barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla*, Setaria spp, *Amaranthus retroflexus, Sida spinosa, Xanthium strumarium* and the like.

EXPERIMENTAL

Plant Growth Conditions

Unless, otherwise indicated, all plants were grown Scotts Metro-Mix™ soil (the Scotts Company) in an environmental growth room at 22° C., 65% humidity, 65% humidity and a light intensity of $\sim 100\,\mu$-E $m^{-2}s^{-1}$ supplied over 16 hour day period.

Seed Sterilization

All seeds were surface sterilized before sowing onto phytagel plates using the following protocol.
1. Place approximately 20–30 seeds into a labeled 1.5 mL conical screw cap tube. Perform all remaining steps in a sterile hood using sterile technique.
2. Fill each tube with 1 mL 70% ethanol and place on rotisserie for 5 minutes.
3. Carefully remove ethanol from each tube using a sterile plastic dropper; avoid removing any seeds.
4. Fill each tube with 1 mL of 30% Clorox and 0.5% SDS solution and place on rotisserie for 10 minutes.
5. Carefully remove bleach/SDS solution.
6. Fill each tube with 1 mL sterile dI $H_2O$; seeds should be stirred up by pipetting of water into tube. Carefully remove water. Repeat 3 to 5 times to ensure removal of Clorox/SDS solution.
7. Fill each tube with enough sterile dI $H_2O$ for seed plating (~200–400uL). Cap tube until ready to begin seed plating.

Plate Growth Assays

Surface sterilized seeds were sown onto plate containing 40 ml half strength sterile MS medium (no sucrose) and 1% Phytagel using the following protocol:
1. Using pipette man and 200 uL tip, carefully fill tip with seeds and 0.1% agarose solution. Place 10 seeds across the top of the plate, about ¼ in down from the top edge of the plate.
2. Place plate lid ¾ of the way over the plate and allow to dry for 30 minutes or until agarose solution is dry. It is important to allow agarose solution to dry completely before sealing up plates in order to prevent contamination.
3. Using sterile micropore tape, seal the edge of the plate where the top and bottom meet.
4. Place plates stored in a vertical rack in the dark at 4° C. for three days.
5. Three days after sowing, the plates transferred into a growth chamber with a day and night temperature of 22 and 20° C., respectively, 65% humidity and a light intensity of $\sim 100\mu$-E $m^{-2}\,s^{-1}$ supplied over 16 hour day period.
6. Beginning on day 3, daily measurements are carried out to track the seedlings development until day 14. Seedlings are harvested on day 14 (or when root length reaches 6 cm) for root and rosette analysis.

Example 1

Construction of a Transgenic Plant Expressing the Driver

The "Driver" is an artificial transcription factor comprising a chimera of the DNA-binding domain of the yeast GAL4 protein (amino acid residues 147) fused to two tandem activation domains of herpes simplex virus protein VP16 (amino acid residues 413–490). Schwechheimer et al. (1998) *Plant Mol Biol* 36:195–204. This chimeric driver is a transcriptional activator specific for promoters having GAL4 binding sites. Expression of the driver is controlled by two tandem copies of the constitutive CaMV 35S promoter.

The driver expression cassette was introduced into *Arabidopsis thaliana* by agroinfection. Transgenic plants that stably expressed the driver transcription factor were obtained.

Example 2

Construction of a Mg-Chelatase CHL H Antisense Expression Cassette in a Binary Vector A DNA corresponding to a 1128 nucleotide fragment of the *A. thaliana* Mg-chelatase CHL H subunit cDNA was ligated into the PacI/AscI sites of the *E.coli*/Agrobacterium binary vector PGT3.2 in the antisense orientation. This placed transcription of the Mg-chelatase CHL H antisense RNA under the control of an artificial promoter that is active only in the presence of the driver transcription factor described above. The artificial promoter contains four contiguous binding sites for the GAL4 transcriptional activator upstream of a minimal promoter comprising a TATA box.

The ligated DNA was transformed into *E.coli*. Kanamycin resistant clones were selected and purified. DNA was isolated from each clone and characterized by PCR and sequence analysis. pPG315 and pPG316 express Mg-chelatase antisense RNA. The antisense expression cassette and a constitutive barnase expression cassette are located between right and left T-DNA borders. Thus, this DNA can be transferred into a recipient plant cell by agroinfection.

Example 3

Transformation of Agrobacterium with the Target Expression Cassette pPG315 and pPG316 were transformed into *Agrobacterium tumefaciens* by electroporation. Transformed Agrobacterium colonies were isolated using Basta selection. Basta resistant colonies were purified. DNA was prepared from such clones and the inserts were amplified by PCR and sequenced to confirm the sequence and orientation. The clones were was stored as a frozen glycerol stock.

Example 4

Construction of Arabidopsis Mg-chelatase Antisense Target Plants

The Mg-chelatase antisense expression cassettes (pPG315 and pPG316) were introduced into *Arabidopsis thaliana* wild type plants by the following agroinfection method. Five days prior to agroinfection, the primary inflorescence of *Arabidopsis thaliana* plants grown in 2.5 inch pots were clipped in order enhance the emergence of secondary bolts.

At two days prior to agroinfection, 5 ml LB broth (10 g/L Peptone, 5 g/L Yeast extract, 5 g/L NaCl, pH 7.0 plus 25 mg/L kanamycin added prior to use) was inoculated with a clonal glycerol stock of Agrobacterium carrying pPG234. The cultures were incubated overnight at 28° C. at 250 rpm until the cells reached stationary phase. The following morning, 200 ml LB in a 500 ml flask was inoculated with 500 µl of the overnight culture and the cells were grown to stationary phase by overnight incubation at 28° C. at 250 rpm. The cells were pelleted by centrifugation at 8000 rpm for 5 minutes. The supernatant was removed and excess media was removed by setting the centrifuge bottles upside down on a paper towel for several minutes. The cells were then resuspended in 500 ml infiltration medium (autoclaved 5% sucrose) and 250 µl/L Silwet L-77™ (84% polyalkyleneoxide modified heptamethyltrisiloxane and 16% allyloxypolyethyleneglycol methyl ether), and transferred to a one liter beaker.

The previously clipped Arabidopsis plants were dipped into the Agrobacterium suspension so that all above ground parts were immersed and agitated gently for 10 seconds. The dipped plants were then cover with a tall clear plastic dome in order to maintain the humidity, and returned to the growth room. The following day, the dome was removed and the plants were grown under normal light conditions until mature seeds were produced. Mature seeds were collected and stored desiccated at 4° C.

Transgenic Arabidopsis T1 seedlings were selected using glufosinate treatment. Approximately 70 mg seeds from an agrotransformed plant were mixed approximately 4:1 with sand and placed in a 2 ml screw cap cryo vial.

The surface of the seeds was sterilized using the chlorine gas method. Briefly, the open vials were placed in a vacuum desiccator in a safety hood. A glass beaker containing 200 ml 5.25% sodium hypochlorite solution was placed in the desiccator. Two ml concentrated HCl was added to the hypochlorite solution and the cover was placed on the desiccator. Vacuum was applied briefly to seal the dessicator, and the seeds were left in the desiccator overnight.

One vial of sterilized seeds was then sown in a cell of an 8 cell flat. The flat was covered with a dome, stored at 4° C. for 3 days, and then transferred to a growth room. The domes were removed when the seedlings first emerged. After the emergence of the first primary leaves, the flat was sprayed uniformly with a 1:3000 dilution of Liberty™ (AgrEvo; 11.3% glufosinate) in water, 0.005% Silwet (50 µl/L) until the leaves were completely wetted. The spraying was repeated for the following two days.

Ten days after the first spraying resistant plants were transplanted to 2.5 inch round pots containing moistened sterile potting soil. The transplants were then sprayed with herbicide and returned to the growth room. These herbicide resistant plants represent stably transformed T1 plants. Two Mg-chelatase target plant lines were obtained for each of the pPG315 and pPG316 constructs. Mature T1 plants were then dried and harvested for T2 seeds.

Example 5

Figure 2:
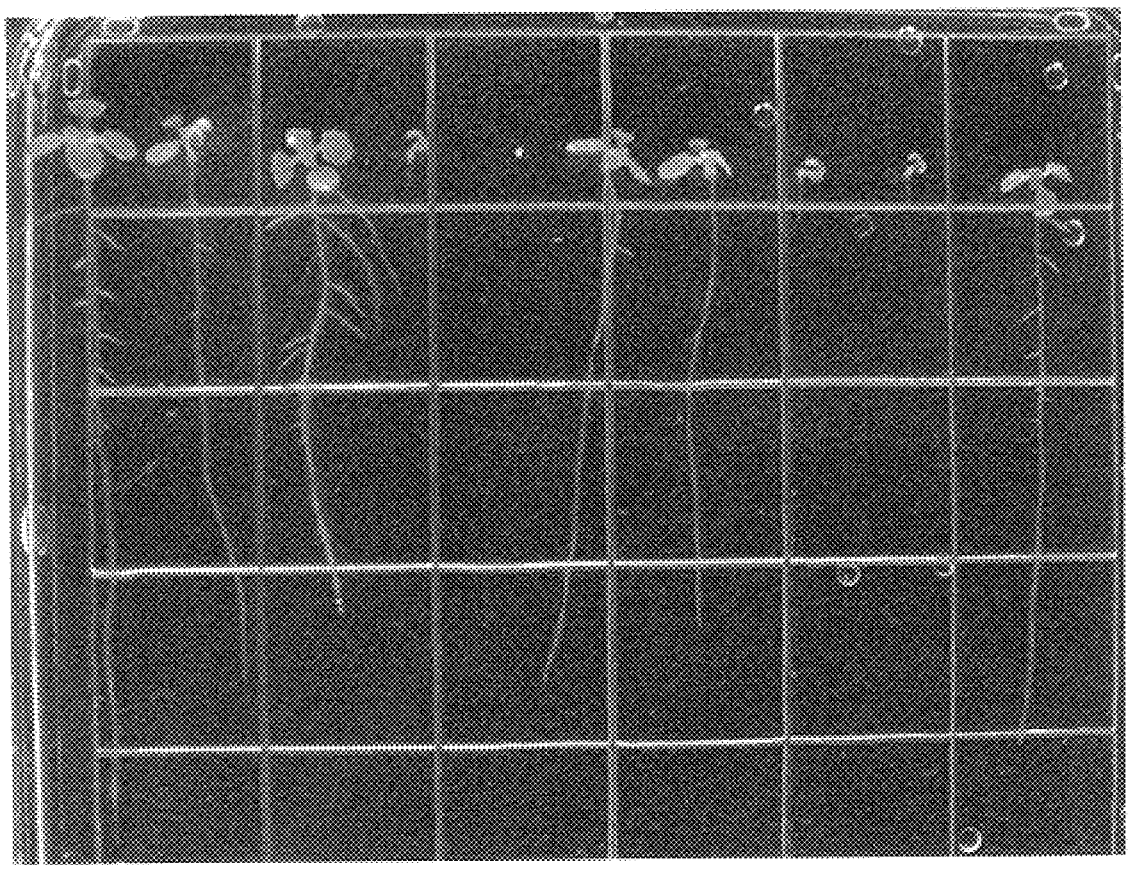
FIG. 2 is a digital image showing the effect of Mg-chelatase CHL H antisense expression on *Arabidopsis thaliana* seedlings.

Effect of Arabidopsis Mg-chelatase Antisense Expression in Arabidopsis Seedlings The Mg-chelatase target plants from three transformed plant lines obtained in Example 4 were crossed with the Arabidopsis transgenic driver line described above. The resulting F1 seeds were then subjected to a PGI plate assay to observe seedling growth over a 2-week period. Seedlings were inspected daily for growth and development. During this period, approximately half of seedlings derived from three Arabidopsis Mg-chelatase antisense target lines developed varying levels of chlorosis (yellowing), abnormal development and significantly impaired growth. FIG. 2 shows the effect of Mg-chelatase CHL H antisense expression on Arabidopsis seedlings. The results are summarized in Table 1.

TABLE 1

Phenotypes of plants expressing Mg-chelatase antisense RNA

| Construct | No. Wild Type | No. Chlorotic/Abnormal | $\chi^2$ Value[a] | Probability[a] |
|---|---|---|---|---|
| PPG315 | | | | |
| line 1 | 5 | 4 | 0.111 | 0.739 |
| line 2 | 4 | 5 | 0.111 | 0.739 |
| PPG316 | | | | |
| line 1 | 4 | 5 | 0.111 | 0.739 |
| line 2 | 10 | 0 | 10.00 | 0.002[b] |

[a]Chi-square and P values (0.05) were obtained to evaluate the hypothesis that chlorosis and wild-type phenotypes are segregating in a 1:1 ratio.
[b]This line clearly does not show segregation of an abnormal phenotype.

The clear 1:1 segregation ratio observed in 3 out of 4 independent Mg-chelatase antisense lines obtained from two independent constructs demonstrates that the antisense expression of this gene results in significantly impaired growth and represents an essential gene from normal plant growth and development. The fact that the progeny derived form one line selected from the pPG316 transformation did not exhibit any abnormal phenotype is not unexpected since it is well known that antisense expression does not work equally well in all independently transformed lines containing the same construct.

While the foregoing describes certain embodiments of the invention, it will be understood by those skilled in the art that variations and modifications may be made and still fall within the scope of the invention.

What is claimed is:

1. A method for identifying a compound as a candidate for a herbicide, comprising:

a) contacting protoporphyrinogen IX and appropriate amounts of $Mg^{2+}$ and adenosine triphosphate (ATP), with Mg-chelatase in the absence of said compound;

b) contacting protoporphyrinogen IX and appropriate amounts of $Mg^{2+}$ and ATP with Mg-chelatase in the presence of said compound; and c) determining the concentration of protoporphyrinogen IX and/or Mg-protoporphyrinogen IX after the contacting of steps (a) and (b);

wherein said Mg-chelatase is from Arabidopsis.

2. The method of claim 1, wherein said Mg-chelatase is from *Arabidopsis thaliana*.

3. The method of claim 1, wherein the concentration of protoporphyrinogen IX is determined.

4. The method of claim 1, wherein the concentration of Mg-protoporphyrinogen IX is determined.

5. The method of claim 4, wherein the concentration of Mg-protoporphyrin IX is determined using a fluorometric assay.

* * * * *